United States Patent [19]

Hobbs et al.

[11] 4,160,205

[45] Jul. 3, 1979

[54] DETECTION OF BACTERIAL ACTIVITY

[75] Inventors: Geoffrey Hobbs; Alfred C. Jason, both of Aberdeen; John C. S. Richards, Old Aberdeen, all of Scotland

[73] Assignee: National Research Development Corporation, London, England

[21] Appl. No.: 843,493

[22] Filed: Oct. 19, 1977

[30] Foreign Application Priority Data

Oct. 19, 1976 [GB] United Kingdom ............... 43334/76

[51] Int. Cl.² ............................................. G01R 27/02
[52] U.S. Cl. ................................ 324/65 R; 23/230 B; 324/71 R; 324/57 R; 435/30; 435/291
[58] Field of Search ............. 324/65 R, 57 R, 58.5 A, 324/71 R; 195/103.5 R; 23/253 R, 230 B

[56] References Cited

U.S. PATENT DOCUMENTS

| | | | |
|---|---|---|---|
| 3,952,246 | 4/1976 | Sprott et al. | 324/58.5 A X |
| 3,984,766 | 10/1976 | Thornton | 324/57 R |

FOREIGN PATENT DOCUMENTS

1299363 12/1972 United Kingdom .................. 324/65 R

*Primary Examiner*—Stanley T. Krawczewicz
*Attorney, Agent, or Firm*—Cushman, Darby & Cushman

[57] ABSTRACT

Bacterial activity is detected by inoculating the bacteria into a suitable nutrient medium and monitoring the resistive component of the electrical impedance of this culture in such a manner that the value obtained is influenced by the temperature coefficient of the resistive component to a degree which is equivalent to a change in temperature of not more than ±0.01 K. Either the temperature of the culture is maintained constant to ±0.01 K and the resistive component is sensed directly, or the resistive component of the culture is compared with the resistive component of a reference volume of the nutrient medium, the temperatures of the culture and the reference volume being maintained constant to ±1.0 K and their difference in temperature being held to ±0.01 K.

16 Claims, 16 Drawing Figures

DETECTION OF BACTERIAL ACTIVITY

This invention relates to the detection of bacterial activity by the determination of the resistive component of electrical impedance.

It is well known that when a metabolizing cell converts complex nutrients into simpler metabolic end products, there is a small change in the complex electrical impedance of the supporting medium mainly due to an increase in the concentration of ions, so that the conductance increases. Measurements of such changes in complex impedance are described by Ur and Brown in the Journal of Medical Microbiology, Volume 8, 1975, pages 19 to 28, and a suitable apparatus is disclosed by Ur in the specification of U.K. Pat. No. 1,299,363.

When complex impedance is measured, the signal is noisy. It is believed that this noise is largely due to variations in the capacitive components of the polarisation impedance of the nutrient medium at the measuring electrodes. The present inventors believe that this problem can be partly overcome by the measurement of only the resistive component of the impedance (or the conductivity). In the specification of UK Pat. No. 1,433,887, Bactomatic Inc., a method of evaluating bacterial growth by conductivity measurements is disclosed. Pairs of identical containers holding the same nutrient medium, one inoculated with bacteria, the other remaining sterile and both in an incubator, are compared. For the electrical arrangement shown in FIG. 3 of that patent, the polarisation impedances in the pair of containers will cancel.

However, it is believed that the problem has still not been fully solved. It is an object of the present invention to provide a method by which the growth of bacteria can be detected at an earlier stage than has previously been possible, and by which the growth rates can be measured accurately; by which bacteria can be counted; and by which, at some time in the future, it may be possible to identify unknown bacteria.

According to the invention a method of detecting bacterial activity comprises inoculating the bacteria into a suitable nutrient medium; maintaining this culture at a substantially constant temperature; and monitoring the resistive component of the electrical impedance of the culture for a period of time sufficient for a change in said resistive component due to metabolizing bacteria to be detectable and in such a manner that the value obtained is influenced by the temperature coefficient of the resistive component to a degree which is equivalent to a change in temperature of not more than $\pm 0.01$ K., preferably not more than $\pm 0.001$ K.

In one method the temperature of the culture is maintained constant to within $\pm 0.01$ K., preferably to within $\pm 0.001$ K., and the resistive component is sensed directly.

In another method said value is obtained by comparing the resistive component of the culture with the resistive component of a reference volume of said nutrient medium, the temperatures of the culture and the reference volume being held constant to within $\pm 1.0$ K., preferably to within $\pm 0.1$ K., and the difference in temperature between the culture and the reference volume being held constant to within $\pm 0.01$ K., preferably to within $\pm 0.001$ K. The reference volume will usually be sterile but in some arrangements the culture may include a growth modifier, usually a growth inhibitor such as an antibiotic, when the reference volume will comprise the same nutrient medium plus bacteria as the culture, but will not contain a growth modifier.

The usually accepted limits of temperature control in bacteriology are $\pm 1.0$ K., and it is believed that it has not previously been realised that much closer control of the temperature of a nutrient medium in which bacteria are metabolizing is essential when bacterial activity is sensed by monitoring the resistive component of impedance. The temperature coefficient of the resistive component of impedance of conventional growth media or nutrients is typically about 0.016 K.$^{-1}$, and it has been found that a change in the number of bacteria of about 30 per cubic millimeter is equivalent to a change in resistive component of about 1 in $10^5$.

For a change in resistive component of this order to be ascribed unambiguously to bacterial activity, the temperature must therefore be stable to within about $0.6 \times 10^{-3}$K. If temperature is controlled to only 1.0 K., then by proportion only changes in resistive component of about 1.6 in $10^2$ can be ascribed to bacterial activity; this is equivalent to about 50,000 bacteria per cubic millimeter. In contrast, if temperature is effectively controlled to $\pm 0.001$ K. according to the invention, then it is possible to detect a change in resistive component due to the division of about 50 bacteria per cubic millimeter.

In the prior art, it has been conventional to use an air incubator to maintain a nutrient medium plus bacteria at a required temperature. In such a device, although a measuring instrument may indicate a temperature which is constant to within $\pm 0.1$ K. as stated by Cady in his aforementioned paper, it has been found that the actual temperature in different parts of the air incubator may vary by 1 K. or more. Further, when the air enclosure is disturbed while specimens are placed in position or removed, large temperature fluctuations have been found to occur. Thus the temperature of specimens in the enclosure is not controlled as closely as a temperature measuring device indicates. The importance of precise temperature control of the nutrient medium itself has now been realised by the present inventors.

It is a further feature of a method according to the present invention that the temperature of the bacterial culture, and of a reference volume of the same nutrient medium if present, is maintained by immersing containers of the culture and reference medium in a bath of a liquid of high thermal conductivity, usually water. Such a bath allows the required degree of temperature control to be attained, and its temperature is barely disturbed when samples are removed or inserted.

The high thermal conductivity ensures that all parts of the bath are kept close to its mean temperature. In a well stirred water bath, whose mean temperature is kept constant to within $\pm 0.001$mk., the temperature differences between two adjacent cells, one sterile and the other inoculated, were estimated to be less than $3 \times 10^{-5}$K., making it possible to detect a change in conductivity corresponding to the division of a single bacterium per cubic millimeter.

It has been suggested in UK Pat. No. 1,433,887 that the overall shape of the growth curves are characteristic of a given bacterial species in a given nutrient medium. Thus as stated in that patent the "comparison of a group of resistance curves for an unknown species of microorganism grown in a series of nutrients with curves of a known species in identical nutrients would reveal the identity of such unknown species since the series of resistance curves are characteristic of that species."

It has now been found that the use of a closely controlled temperature system provides the further result that mathematical constants associated with a single growth curve are characteristic of a particular bacterial strain in a particular nutrient medium. Thus temperature control within the limits according to the invention allows characterisation of a bacterial species by one or more of the mathematical constants associated with a single curve, which may be composed of one or more exponential phases, instead of by comparing the general shapes of families of growth curves.

Also according to the invention, a method of detecting bacterial activity further comprises monitoring the resistive component of the electrical impedance of the culture over a period of time sufficient for at least a first exponential variation in said resistive component to be detectable.

The invention further comprises apparatus suitable for carrying out a method according to the invention.

Of the drawings filed with this specification, the prior art will be described with reference to FIG. 1 and the invention will be described by way of example with reference to FIGS. 2 to 13 in which.

Figure 1:
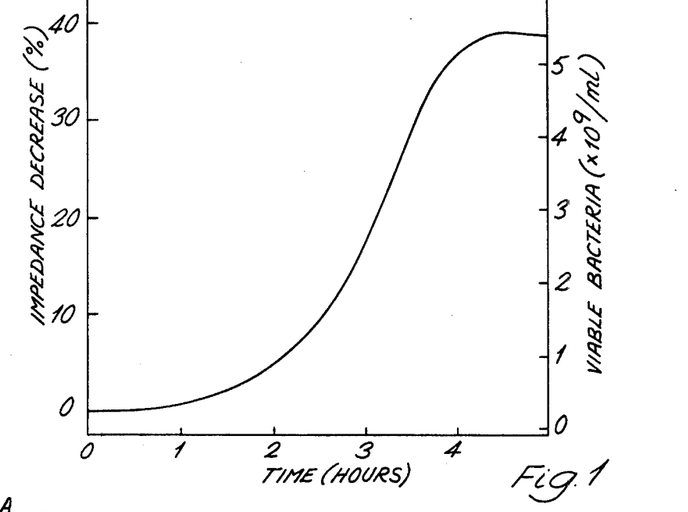

Referring now to FIG. 1 which is reproduced from page 83 of the aforementioned paper by Cady, the figure relates to the growth of $10^8$ *Escherichia coli* (*E.coli*) in 0.5 milliliters of tripticase soy broth held at a temperature of 37° C. in an incubator "designed to hold its temperature to less than 0.1° C.". The Figure shows the variation with time of the percentage decrease in the complex impedance after inoculation, measured at 2 kilohertz and 100 millivolts. It can be clearly seen that no activity can be detected for almost an hour. This has been previously considered to be an inherent "lag" time during which no growth takes place in any bacterial system. Further, as has already been explained, it is probable that the temperature of different parts of the air incubator varied, especially when the specimens were placed in position.

Figure 2:
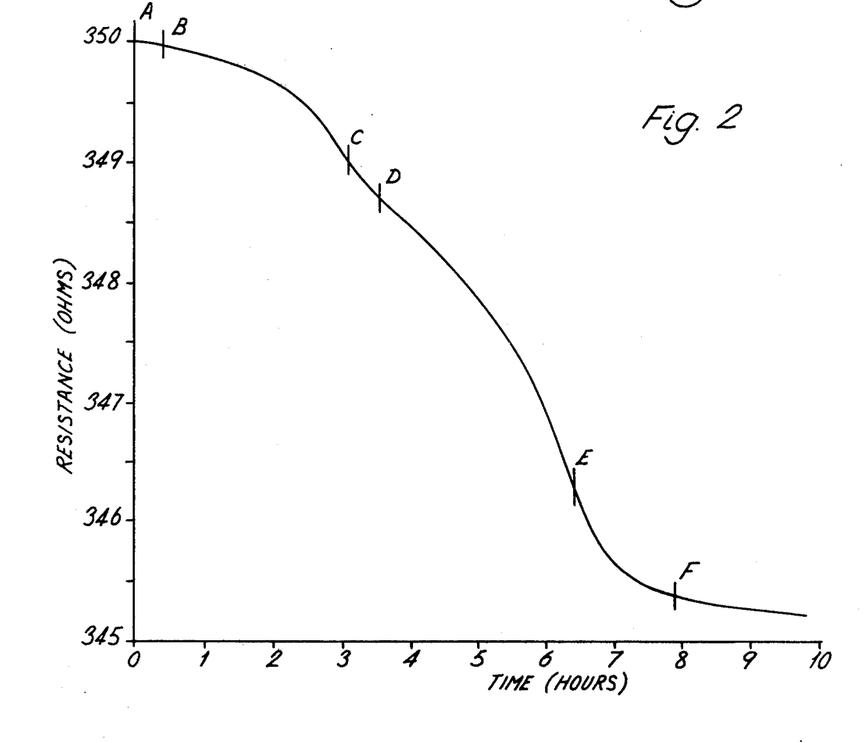
FIG. 2 illustrates the variation with time of the resistive component of the electrical impedance of a culture of *E.coli* monitored according to the ivention.

FIG. 2 illustrates the variation of the resistive component of impedance of a culture of *E.coli* at an initial concentration of $10^5$ organisms per milliliter, in C.M.1 broth in a measuring cell immersed in a water bath so that the broth is kept at a temperature which is constant to within ± 0.001 K.; the measurement was made between platinum electrodes and at 10 kHz. The applied voltage was 0.1 volt, which is below the potential threshold at which electrochemical reactions begin.

In marked contrast to the curve in FIG. 1, exponential growth is already detected at the point B even though the number of bacteria present was smaller by a factor of $10^3$. This also indicates that the inherent "lag" time is much shorter than was previously believed to be the case. There may be a small initial disturbance at the time of inoculation, but it has been found that inoculation with live bacteria, even at concentrations higher than 1000 per cubic millimeter, causes a change in conductance which is negligible compared with the changes due to subsequent multiplication of the bacteria.

These results have been obtained by reason of the much closer control of the actual temperature of the bacterial culture than has previously been used, allowing very small changes in the resistive component of impedance to be detected.

In FIG. 2, the curve can be seen to be in the form of an initial decrease AB, followed by two further decreasing sections, BC and DE, of exponential form and corresponding to two periods of growth at different rates, with a transition section, CD, in which some bacteria are in each state, and with a final steady growth rate FG after a second transitional period EF.

This double-exponential growth rate curve has not previously been detected by impedance measurements. It is believed that each bacterial type has a characteristic curve with different exponential constants and with the first transition section CD always occurring after a characteristic decrease in the resistive component of impedance. To observe such curves in an impedance-measuring system, the resistive component must be measured according to the present invention. In some systems there is only one exponential curve, in other systems there are two or more exponential curves.

Figure 3:
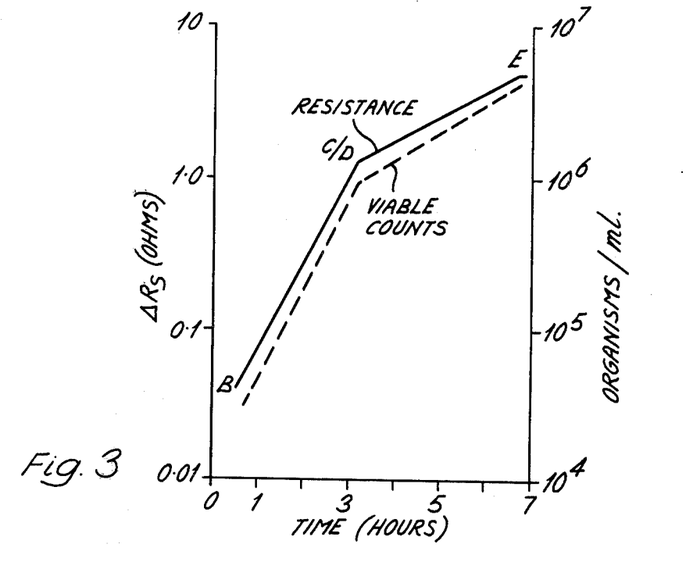
FIG. 3 illustrates the variation with time of the change in the resistive component shown in FIG. 2 and the corresponding changes in bacterial numbers.

In FIG. 3 the full line is a plot on a logarithmic scale of the change in resistive component against time for the curve shown in FIG. 2. The two exponential sections have different constants and therefore different slopes in FIG. 3. For *E.coli* the generation time, which is derived from the time constant of the first exponential part BC of the curve, is 0.42 hours. In FIG. 3, the number of organisms present is indicated by the broken line; the results were obtained using a conventional plating technique.

It is believed that the parameters of the two exponential parts of the curve are different for, and therefore, characteristic of, different bacterial strains in particular growth media. It may therefore be predicted that, in the future when measurements of the constants have been made by a method according to the invention, an unknown bacterial species may be identified by determining one or more of the characteristic constants and referring to a table of constants.

Figure 4:
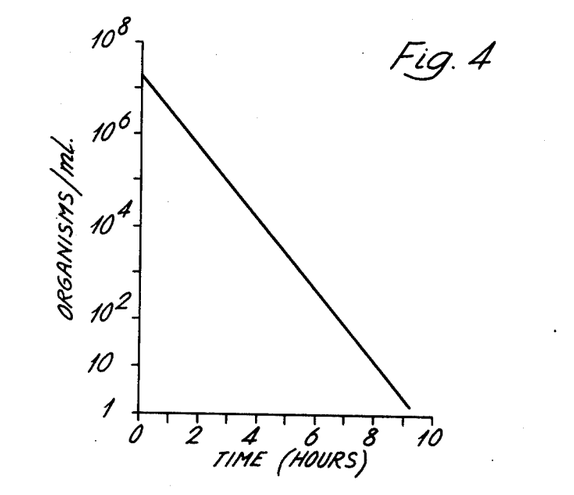
FIG. 4 illustrates the variation with initial bacterial concentration of the time at which the change of resistance in FIG. 3 reaches an arbitrary value of 1 ohm.

Other constants can be obtained. For example in FIG. 2 the change of slope in the region CD always occurs at the same change in resistance for each bacterial species growing in a given medium, corresponding to a characteristic bacterial concentration. Both Ur and Brown and Cady showed that the time at which the impedance changes by a given amount is longest at low numbers of organisms in the inoculum and increases linearly with increase of the logarithm of the numbers. FIG. 4 shows a similar relationship when the resistive component of impedance is measured as in the present invention. Other constants are the assymptotes in directions parallel to the time axis in the regions B and C.

Yet another advantage of the method according to the invention is that it is capable of detecting a change in the resistive component of impedance which corresponds to a bacterial concentration several decades lower than can be counted conveniently to a reasonable level of accuracy by plating techniques.

Figure 5:
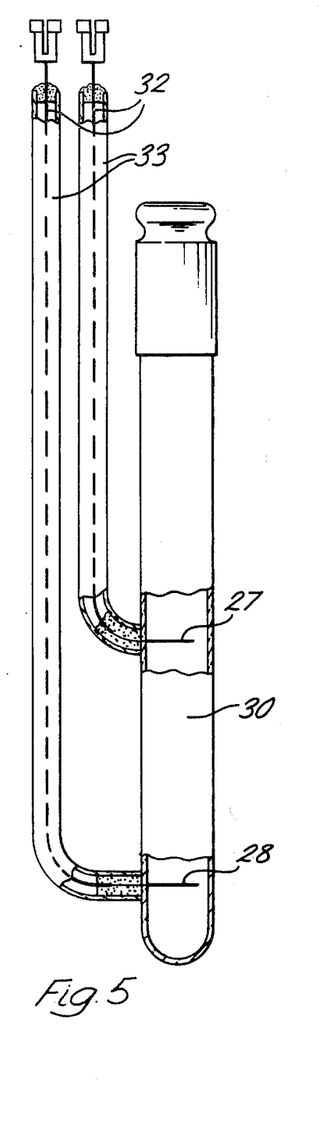
FIG. 5 illustrates a suitable measuring cell.

The required accuracy of control of the temperature of the bacterial culture can, with care, readily be achieved by means of a thermistor bridge controlling the electrical power applied to heat a well stirred, insulated water bath. A container suitable for use in a water bath is shown in FIG. 5. Two platinum electrodes 27, 28 are arranged to be parallel and project across the axis of a standard soda glass test tube 30 at a separation of about 50 millimeters. The electrodes are fused through the test tube wall and connected by copper leads 32 to an electrical measuring circuit (not shown); the leads are insulated from the surrounding water bath (not shown) by glass capillary tubes 33 fused to the test tube at the point of entry of the electrodes.

Figure 6A:
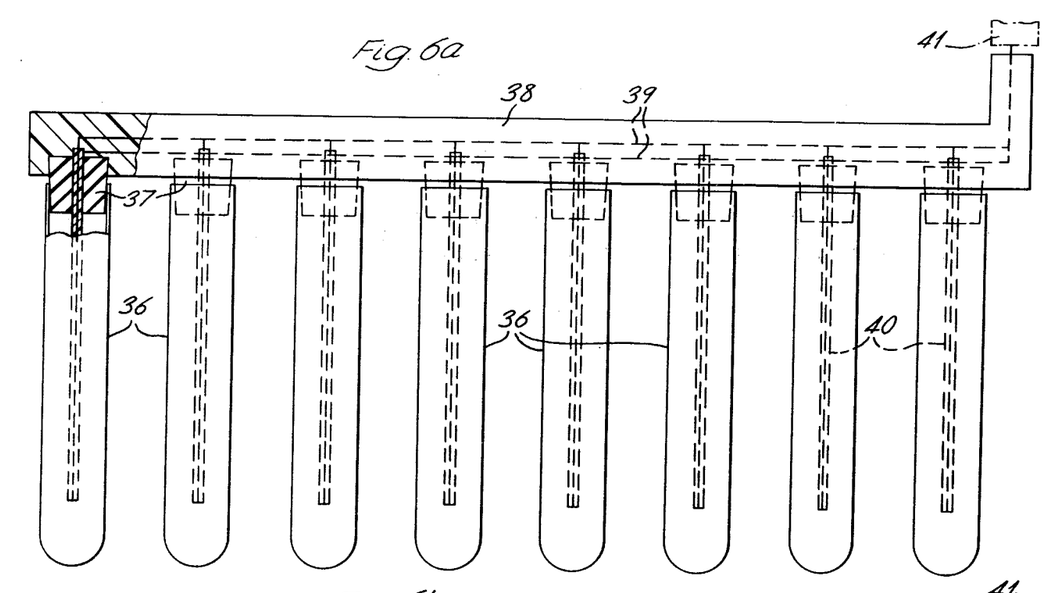
FIGS. 6(a) and 6(b) show in vertical and horizontal section a multiple measuring cell arrangement.
Figure 6B:
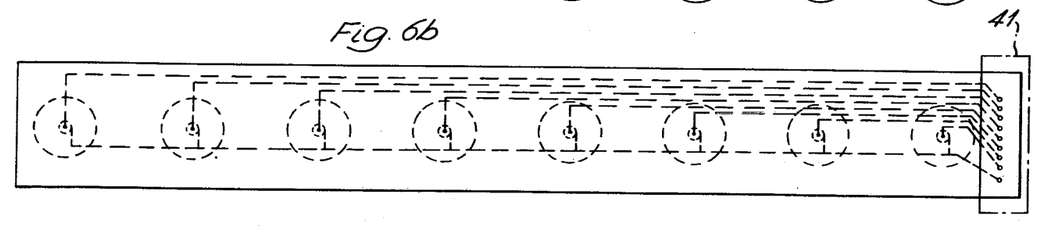

When measuring bacterial activity, it is usually the case that a large number of specimens need to be tested, and it is a further advantage of a method according to the invention that measurements can be made on a multiplicity of samples. To facilitate such measurements, instead of the single measuring cell illustrated in FIG. 5, an arrangement such as that in FIG. 6 may be used.

FIG. 6(a) shows in vertical section a row of test tubes 36 each supported by a tapered stopper 37 fixed to the lower side of a plastic strip 38 which encloses connecting wires 39. Each stopper supports a coaxial electrode probe 40, shown in detail in FIGS. 7(a) and 7(b). As shown in FIG. 6(b), one electrode from each coaxial probe 40 is connected via a wire to the common pin of a multiple connector 41, and the other electrode is connected to one of the individual pins in the connector 41. This arrangement is convenient for matrix switching to a common measuring circuit.

Figures 7A, 7B:
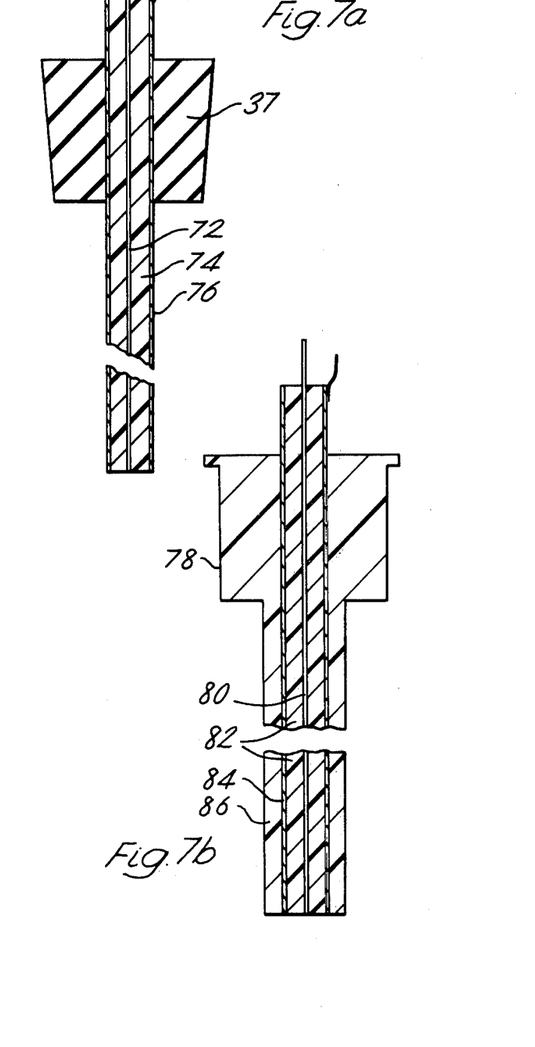
FIGS. 7(a) and 7(b) show alternative coaxial probes for use in a multiple measuring cell.

Two alternative coaxial probes are shown in FIGS. 7(a) and 7(b). In FIG. 7(a) a tapered stopper 37 supports a tinned copper wire 72 insulated by polytetrafluoroethylene (p.t.f.e.) sheath 74 covered on its curved sides by a platinum plated copper sheath 76. The end of the wire 72 is level with the ends of the sheaths 74, 76 and is platinum plated. In FIG. 7(b) a polypropylene insert 78 supports a tinned copper wire 80, and a ptfe sheath 82 surrounded by a copper sheath 84, which in this embodiment is insulated by a polypropylene outer sheath 86. The ends of the copper wire 80 and the copper sheath 84 are level with the insulating sheaths 82, 86 and are platinum plated. Such probes can be repeatedly sterilised by autoclaving.

A water bath (not shown) suitable for controlling the temperature of the test tubes may be made from 1.5 millimeters thick stainless steel, and measure $600 \times 300 \times 300$ millimeters, insulated by 100 millimeter thick slabs of expanded polystyrene. The water is preferably circulated vigorously by a pump impeller with the pump motor outside the insulating slabs. A single 300 watt ceramic sheathed heater is adequate to maintain the temperature of the water at 37° C. at all normal laboratory temperatures.

Figure 8:
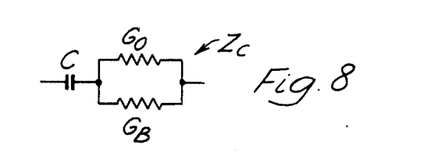
FIG. 8 is an electrical representation of a bacterial culture.

Considering now some suitable electrical circuits for measuring the resistive component of electrical impedance, the impedance of a container or cell containing a bacterial culture may be represented, as shown in FIG. 8, as a capacitance C in series with a conductance G. The capacitance arises mainly from polarisation at the electrode/liquid interface, which is typically 1 or 2 microfarads at 10 kilohertz. The conductance comprises the conductance $G_o$ of the sterile nutrient medium, typically 3 millisiemens but possibly between 1 and 20 millisiemens. The values of C and $G_o$ do not vary by more than ±20% between measuring cells of the same nominal geometry filled with the same growth medium. The effect of bacterial multiplication is represented by the conductance $G_B$, which is often less than 100 microsiemens.

The complex impedance of the cell in this representation at an angular frequency $w = 2\pi f$ is:

$$Z_c = 1/(G_o + G_B) + 1/Cjw \quad (1)$$

Changes in $G_B$ occurring over a period of up to several days must be observed with, if possible, a resolution of better than 0.1 microsiemens and an accuracy of about 1%.

Figure 9A:
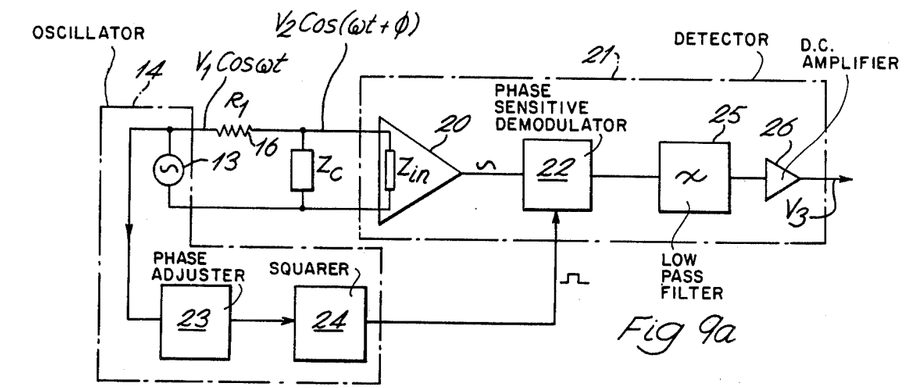
FIGS. 9(a), 9(b), 9(c) and 9(d) illustrate electrical circuits suitable for use in monitoring a bacterial culture according to the invention.

A suitable measuring circuit as shown in FIG. 9(a) in which the cell, referenced $Z_c$, is supplied with power by a 10 kHz source 13 through a resistor 16, and is connected across a very high input impedance a.c. amplifier 20. The amplifier output is connected to a phase sensitive demodulator 22 which is supplied with square waves by a squarer 24 which is also powered by the source 13 through a phase adjuster 23. The output of the demodulator is connected through a low pass filter 25 and d.c. amplifier 26 to a digital voltmeter or analogue recorder such as a data logger or a chart recorder (not shown). The source 13, phase adjuster 23 and squarer 24 will be referred to as the oscillator 14. The amplifier 20, demodulator 22, filter 25 and amplifier 26 will be referred to as the detector 21.

If the output of oscillator 14 is represented by $V_1 \cos\omega t$, the input to detector 21 can be represented as $V_2 \cos(\omega t + \phi)$. If $A_D$ is the conversion gain of the detector 21, then the d.c. output $V_3$ of the detector 21 is:

$$V_3 = A_D V_2 \cos\phi \quad (2)$$

If $R_1 >> |Z_C|$, $$\text{then } V_3 = \frac{A_D V_1}{R_1} |Z_c| \cos\phi$$

$$= \frac{A_D V_1}{R_1} (G_o + G_B)$$

If $G_o >> G_B$, $$\text{then } V_3 = \frac{A_D V_1}{R_1} \left( \frac{1}{G_o} - \frac{G_B}{G_o^2} \right) \quad (3)$$

Alternatively the cell can be represented by its admittance $Y_c$ where:

$$Y_c = \frac{1}{Z_c} = \left( \frac{G_o + G_B + jd^2 C\omega}{(1 + d^2)} \right) \quad (4)$$

-continued where $d = \dfrac{G_o + G_B}{C\omega}$

Figure 9B:
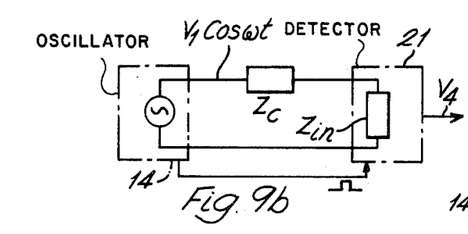

The real part of $Y_c$ can be measured with the circuit of FIG. 9(b) where the detector 21 is similar to that of FIG. 9(a) except that series feedback is used to make the input impedance of the amplifier $<<Z_c$. The detector 21 is therefore best described by its conversion transfer resistance $R_D$, which is proportional to the gains of the amplifiers 20 and 26 and the efficiency of the demodulator 22. If the input current is $I_1 \cos(t+\phi')$, the DC output voltage is given by $$V_4 = I_1 R_D \cos\phi' \qquad (5)$$
$$= V_1 R_D (G_o + G_B)/(i + d^2)$$
$$= V_1 R_D (G_o + G_B) \text{ when } d^2 << 1$$

In the worst case, with $C=1\mu F$ and $G_o=20$ mS, $d^2$ can be as large as 0.1, but it is more typically $<0.001$ and does not affect the measured change in conductance significantly.

Figure 9C:
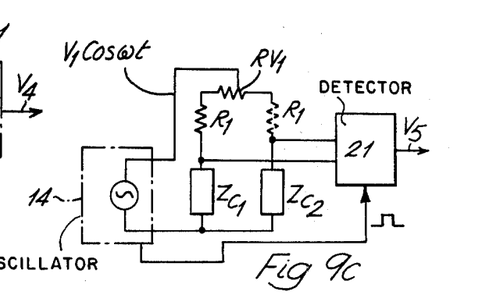

It is desirable to detect the levels of growth corresponding to a change in conductance of the cell containing the culture as small as 1 part in $10^5$ occurring over a period of hours, and the systems of FIG. 9(a) and (b) must have very stable parameters ($V_1$, $A_D$, $R_D$ etc.) and very small zero drifts if such small changes are to be reliably observed. These requirements can be greatly eased by balancing the cell containing the culture against a similar cell containing only the growth medium; this is shown in the resistance bridge of FIG. 9(c) and the transformer ratio conductance bridge of FIG. 9(d); again the oscillator 14 and the detector 21 are used; if the two cells are in the same environment, the effects of temperature changes are greatly reduced. The output from the detector 21 is initially set to zero by adjusting the fine balance potentiometer RV1 or RV2, and the output is subsequently given by:

(1) for the resistance bridge of FIG. 9(c)

$$V_5 = -(V_1 A_D/R_2)(G_B/G_o^2) \qquad (6)$$

assuming $G_B >> G_o$.

Figure 9D:
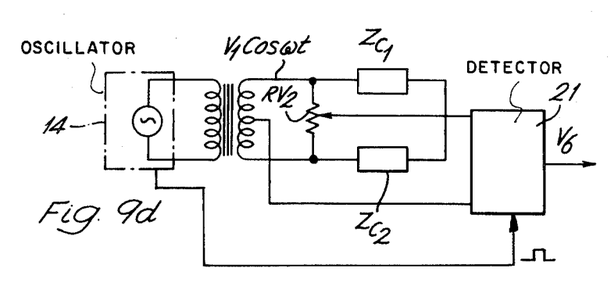

(2) for the conductance bridge of FIG. 9(d)

$$V_6 = V_1 R_D G_B \qquad (7)$$

assuming $d^2 << 1$.

When only a few samples ($<10$, say) are to be measured at one time the transformer ratio admittance bridge of FIG. 9(d) is preferable; it allows $G_B$ to be presented directly on a chart recorder. Only when $d(=C\omega/G_o)$ is exceptionally large does there seem to be any advantage in the impedance bridge of FIG. 9(c); it does not give $G_B$ directly, and it needs a good differential AC amplifier.

It is advantageous to arrange the measuring circuit to sense the resistive component of impedance of a series RC circuit (representing a bacterial culture) because the resistive component is then essentially independent of the capacitive part. In a parallel RC circuit, the resistive component may include a contribution from the capacity, depending on the measuring frequency, and this (polarisation) capacity will be subject to fluctuations, which at present cannot be explained. Balancing the measuring cell against a reference cell does not necessarily eliminate the fluctuations. This is a disadvantage of prior art apparatus. The circuits shown in FIGS. 9(a) and 9(b) are therefore preferred to those in FIGS. 9(c) and 9(d), although the latter may be useful in some circumstances.

When a large number of samples is to be measured, e.g. greater than 10, it is convenient to connect each sample in turn to a single measuring system, by means of a multiple switch or switches.

Figure 10:
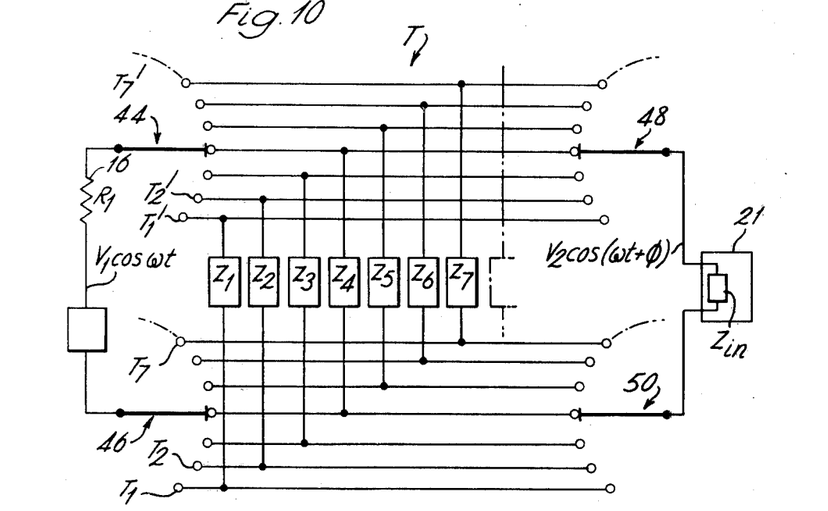
FIG. 10 illustrates the principle of use of ganged switches to reduce the effect of a change in switch resistance.
Figure 11:
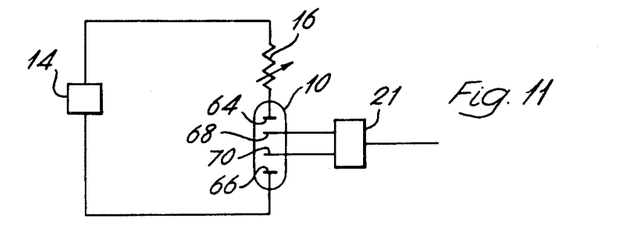
FIG. 11 illustrates a modification to the circuit shown in FIG. 9(a) if a four-terminal measuring circuit is used.

Small changes in resistance, of the order $10^{-2}$ ohms, are significant in a method according to the invention, so that a varying switch resistance may affect the measurements. The influence of such an effect must therefore be eliminated and a switching arrangement such as that shown in FIG. 10 has been found to be advantageous. The illustration uses the circuit arrangement shown in FIG. 9(a) in combination with a number of individual cells. The complex impedance of the bacterial cultures in the individual cells 36 are represented as $Z_1$ to $Z_7$, and the pair of electrodes immersed in each culture are connected to a different pair of terminals $T_1$; $T_1'$ to $T_7$; $T_7'$ of a multiple way switch. The oscillator 14 and resistor 16 are connected through a first pair 44, 46 of four ganged switches, and the detector 21 is connected through a second pair 48, 50 of the ganged switches, to the multiple way switch T. It is an advantage of the arrangement that the resistances of the switches 44, 46, 48, 50 and T are effectively in series with resistor 16 or with the input impedance of detector 21. Since the resistance and input impedance can both be made very large, a change in switch resistance even of 10 ohms may have a negligible effect on the measurements of resistive component of the impedance, provided the variations in the on-resistance of the switch are negligible compared with $R_1$ or $|Z_{in}|$ in FIG. 9(a).

It is possible to use a modified cell matrix and a modified automatic switching arrangement in conjunction with a suitable bridge, such as that of FIG. 9c, to compare the resistances of a pair of cells connected into circuit simultaneously.

However, in a suitable environment, such as a water bath, any changes common to the reference cell and the inoculated cell arising for example from temperature changes normally occur slowly and are small over a period of say one minute. Nearly all of the advantages which result from having two cells simultaneously in a suitable bridge circuit can be obtained by presenting in turn to the impedance measuring apparatus a reference cell and an inoculated cell. A digital computing system stores the resistance of each cell as it is measured. Any changes in the measured resistance of the reference cell can then be used to correct automatically the measured resistance of the inoculated cell and make available for further computation the corrected resistance of the cell. For example, if the measured resistance of the reference cell on successive readings taken say ten minutes apart are $R_F$ and $R_F + r_F$ and the measured readings of the inoculated cell were $R_I$ and $R_I + r_I$, then a suitably programmed computer would calculate the change to be ascribed to bacterial activity in resistance of the inoculated cell as $$R_B = \frac{(R_I + r_I)R_F}{(R_F + r_F)} - R_I = \frac{R_I(1 + r_I/R_I)}{1 + r_F/R_F} - R_I$$

If both reference and inoculated cell change by the same percentage, $R_B$ is zero. This technique corrects for any change in the sensitivity of the measuring apparatus.

With this method it is not essential to have one reference cell for each inoculated cell—in a system with 128 cells only one need be a reference cell provided the remaining cells are filled with reasonably similar growth media and provided any temperature change occurring over a period of several minutes is not significant. If every sixteenth cell is made a reference cell, then the period over which the temperature must be constant is reduced to about half a minute and it is possible to accommodate up to eight dissimilar types of growth media, while still having 120 cells out of 128 inoculated.

Only rarely is a more sensitive instrument required, but when the greatest possible freedom from temperature and any other disturbing influence is required, the balanced system of FIG. 9(d) can be used. In a multichannel instrument, a separate detector is required for each channel, although a common oscillator can be used. This technique is only suitable when relatively few (<10 say) channels are required etc.

The invention has been described with reference to measurements of the resistive component of impedance using two terminal measurements. This has the advantage of simplicity but it is also possible to use a four terminal measuring arrangement, which would eliminate the effects of interfacial polarisation so that measurements at lower frequencies could be made if required.

A modification to the measuring arrangement illustrated in FIG, 9(a) is shown in FIG. 13. The bacterial culture in cell 10 has four electrodes in contact with it. An alternating voltage is applied to the culture by electrodes 64, 66 which are connected in series with the resistor 16 and the oscillator 14, but the impedance measurements are made through two additional electrodes 68, 70, connected to the detector 21.

Modifications to the switching circuits would be required if a four-terminal measuring system were used in conjunction with a matrix array of measuring cells.

A method of determining bacterial activity according to the invention may be used to measure microbial growth in general, for example to determine growth rates, generation times in both batch and continuous culture and growth in the presence of an inhibitor such as an antibiotic. Also, cell numbers and cell mass may be determined. The method may also be used to study any activity leading to a change in resistance of a medium, for example enzyme reactions, chemical reactions, ion release and transfer, membrane permeability, virus and phage propagation and proliferation, sporulation and germination.

It is a further advantage of a method according to the invention that measurements of bacterial growth in nutrient media with wide variations in salt concentration can be made. This is because the sensitive method according to the invention can make measurements on cells having a resistance as low as 50 ohms, but usually about 300 ohms.

Particular applications are the determination of the bacterial load in foodstuffs, either after maceration as used at present, or by taking capillary samples which may give sufficient bacteria for the more sensitive method of the invention to be applied. There are also many possible applications in hospitals, such as investigations of infections in urine and in blood samples.

We claim:

1. A method of detecting bacterial activity comprising inoculating the bacteria into a suitable nutrient medium; maintaining this culture at a substantially constant temperature; and monitoring the resistive component of the electrical impedance of the culture for a period of time sufficient for a change in said resistive component due to metabolising bacteria to be detectable and in such a manner that the value obtained is influenced by the temperature coefficient of the resistive component to a degree which is equivalent to a change in temperature of not more than ±0.01K.

2. A method according to claim 1 in which the temperature of the culture is maintained constant to ±0.01K. and the resistive component is sensed directly.

3. A method according to claim 1 in which said value is obtained by comparing the resistive component of the culture with the resistive component of a reference volume of said nutrient medium, the temperatures of the culture and the reference volume being held constant to ±1.0K., and the difference in temperature between the culture and the reference volume being held constant to ±0.01K.

4. A method according to claim 3 in which there are a plurality of cultures, and the resistive component of each culture in turn is compared with the resistive component of said reference volume, the temperatures of the cultures and of the reference value being held constant to ±1.0K., and the difference in temperature between each culture and the reference volume being held constant at ±0.01K.

5. A method according to claim 1 further comprising monitoring said resistive component over a period of time sufficient for at least a first exponential variation in said resistive component to be detectable.

6. A method according to claim 1 in which said resistive component is monitored in such a manner that the value obtained is influenced by the temperature coefficient of the resistive component to a degree which is equivalent to a change in temperature of not more than ±0.001K.

7. A method according to claim 1 in which the temperature is controlled by immersion of the culture and the reference volume when present in suitable containers in a bath of a liquid of high thermal conductivity.

8. A method according to claim 7 in which the temperature of said liquid is sensed by a thermistor connected in an electrical bridge circuit, said circuit being arranged to control an electrical heating means arranged to heat said liquid.

9. Apparatus for carrying out a method according to claim 2 comprising a measuring cell for containing the culture; means for maintaining the culture at a temperature which is constant to ±0.01K.; and monitoring means for monitoring the resistive component of the electrical impedance of the culture.

10. Apparatus according to claim 9 in which the monitoring means comprises an electrical circuit arranged to measure the resistance of a series combination of a resistor and a capacitor.

11. Apparatus according to claim 9 in which the monitoring means comprises an electrical circuit arranged to measure the conductance of a series combination of a resistor and a capacitor.

12. Apparatus according to claim 9 further comprising a plurality of measuring cells each having two measuring electrodes; a source of alternating current; at least one multiposition switch in series with the source and arranged to connect the source across the electrodes of any selected mesuring cell; and at least one further multiposition switch in series with the monitoring means and arranged to connect the monitoring means across the same selected measuring cell.

13. Apparatus according to claim 9 further comprising a plurality of first electrical conductors and a plurality of second electrical conductors all insulated from each other and arranged to form a matrix; a plurality of measuring cells each having a first measuring electrode connected to one of the first electrical conductors and a second measuring electrode connected to one of the second electrical conductors; a source of alternating current; at least one multiposition switch arranged to connect said source selectively to each first electrical conductor; and at least one further multiposition switch arranged to connect said monitoring means selectively to each second electrical conductor.

14. Apparatus for carrying out a method according to claim 3 comprising a measuring cell for containing the culture; a reference cell for containing the reference volume; means for maintaining the culture and the reference volume at a temperature which is constant to $\pm 1.0$K. and at tempertures which differ by not more than $\pm 0.01$K.; and monitoring means comprising an electrical bridge circuit in which the resistive component of the culture is compared with the resistive component of the reference volume.

15. Apparatus according to claim 14 in which the bridge circuit is a resistance bridge.

16. Apparatus according to claim 14 in which the bridge circuit is a transformer ratio conductance bridge.

* * * * *